US 6,565,359 B2

(12) United States Patent
Calhoun et al.

(10) Patent No.: US 6,565,359 B2
(45) Date of Patent: *May 20, 2003

(54) REMOTE COMPUTER-IMPLEMENTED METHODS FOR COGNITIVE AND PERCEPTUAL TESTING

(75) Inventors: Barbara Calhoun, El Cerrito, CA (US); Bret E. Peterson, Lafayette, CA (US); Michael M. Merzenich, San Franciso, CA (US)

(73) Assignee: Scientific Learning Corporation, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/492,259

(22) Filed: Jan. 27, 2000

(65) Prior Publication Data

US 2003/0059759 A1 Mar. 27, 2003

Related U.S. Application Data

(63) Continuation-in-part of application No. 09/241,362, filed on Jan. 29, 1999, now Pat. No. 6,280,198.

(51) Int. Cl.[7] ................................................ G09B 19/00
(52) U.S. Cl. ...................... 434/236; 434/350; 434/258; 600/300
(58) Field of Search ............................. 434/236, 350, 434/322, 323, 258; 600/300

(56) References Cited

U.S. PATENT DOCUMENTS

| 5,692,906 A | * | 12/1997 | Corder .................... 434/156 X |
| 5,711,671 A | | 1/1998 | Geeslin et al. |
| 5,722,418 A | * | 3/1998 | Bro ......................... 600/545 X |
| 5,724,987 A | * | 3/1998 | Gevins et al. ............ 600/544 X |
| 5,725,472 A | | 3/1998 | Weathers |
| 5,755,576 A | * | 5/1998 | Dunn et al. ............. 434/258 X |

(List continued on next page.)

FOREIGN PATENT DOCUMENTS

| EP | WO 87/07969 | 12/1987 | ............ G06F/15/42 |
| EP | WO 92/13487 | 8/1992 | ............ A61B/5/16 |
| EP | WO 95/29447 | 11/1995 | ............ G06F/15/02 |
| WO | WO 87/07969 | 12/1987 | |
| WO | WO 92/13487 | 8/1992 | |
| WO | WO 95/29447 | 11/1995 | |

OTHER PUBLICATIONS

R.F. White, et al., "Validation of the NES2 in Patients with Neurologic Disorders," *Neurotoxicology and Teratology*, vol. 18, No. 4, pp. 441–448, 1996.

(List continued on next page.)

*Primary Examiner*—S. Thomas Hughes
*Assistant Examiner*—Chanda L. Harris
(74) *Attorney, Agent, or Firm*—Beyer Weaver & Thomas LLP

(57) ABSTRACT

The present invention relates to a computer-implemented methods and apparatus for remote cognitive and/or perceptual testing using a computer network having a remote computer geographically separate from an administering computer. The remote cognitive and/or perceptual testing includes administering a set of cognitive and/or perceptual tests, obtaining a performance response of the person to the tests and uploading the testing information via the computer network. The tests may be administered a number of times to evaluate one or more cognitive skills and/or perceptual abilities. Parallel to the testing, a therapy may be administered. The method may also include monitoring the performance of the person on the tests. The computer-implemented method may additionally include administering a set of initial tests before therapy inception to assess a person's intrinsic cognitive skills and/or perceptual abilities. The results of the initial testing and testing during therapy may be entered into a database. The database may be built from the performance response of multiple people and may be useful in predicting efficacy of a proposed therapy.

27 Claims, 6 Drawing Sheets

U.S. PATENT DOCUMENTS

| | | | | |
|---|---|---|---|---|
| 5,806,522 A | * | 9/1998 | Katims | 600/544 X |
| 5,810,747 A | * | 9/1998 | Brudny et al. | 600/595 X |
| 5,813,863 A | * | 9/1998 | Sloane et al. | 434/236 X |
| 5,879,163 A | * | 3/1999 | Brown et al. | 434/236 X |
| 5,888,074 A | * | 3/1999 | Staplin et al. | 434/258 X |
| 5,911,581 A | | 6/1999 | Reynolds et al. | |
| 5,919,046 A | * | 7/1999 | Hull | 434/258 X |
| 5,940,801 A | | 8/1999 | Brown | |
| 5,957,699 A | | 9/1999 | Peterson et al. | |
| 5,960,403 A | * | 9/1999 | Brown | 705/2 X |
| 5,961,332 A | | 10/1999 | Joao | |
| 5,967,789 A | * | 10/1999 | Segel et al. | 434/236 X |
| 6,027,217 A | * | 2/2000 | McClure et al. | 351/224 X |
| 6,030,226 A | | 2/2000 | Hersh | |
| 6,052,512 A | | 4/2000 | Peterson et al. | |
| 6,053,739 A | | 4/2000 | Stewart et al. | |
| 6,063,028 A | | 5/2000 | Luciano | |
| 6,159,014 A | * | 12/2000 | Jenkins et al. | 434/169 X |
| 6,168,562 B1 | * | 1/2001 | Miller et al. | 600/300 X |
| 6,201,948 B1 | * | 3/2001 | Cook et al. | 434/350 X |
| 6,231,344 B1 | * | 5/2001 | Merzenich et al. | 434/236 |
| 6,234,965 B1 | * | 5/2001 | Miller et al. | 600/300 X |
| 6,280,198 B1 | * | 8/2001 | Calhoun et al. | 434/236 X |
| 6,319,207 B1 | * | 11/2001 | Naidoo | 600/559 X |
| 6,322,521 B1 | * | 11/2001 | Hou | 600/559 X |
| 6,334,778 B1 | * | 1/2002 | Brown | 434/258 X |
| 6,383,150 B1 | * | 5/2002 | Stewart et al. | 600/595 X |
| 6,402,520 B1 | * | 6/2002 | Freer | 434/236 X |

OTHER PUBLICATIONS

R. Letz, et al., "Development of a Computer–Based Battery Designed to Screen Adults for Neuropsychological Impairment," *Neurotoxicology and Teratology,* vol. 18, No. 4, pp. 365–370, 1996.

B. T. Stollery, "The Automated Cognitive Test (ACT) System," *Neurotoxicology and Teratology,* vol. 18, No. 4, pp. 493–497, 1996.

P.J. Fray and T.W. Robbins, "CANTAB Battery: Proposed Utility in Neurotoxicology," *Neurotoxicology and Teratology,* vol. 18, No. 4, pp. 499–504, 1996.

A.M. Williamson, "Historical Overview of Computerized Behavioral Testing of Humans in Neurotoxicology," *Neurotoxicology and Teratology,* vol. 18, No. 4, pp. 351–357, 1996.

T.W. Robbins, et al., "Cambridge Neuropsychological Test Automated Battery (CANTAB): A Factor of Analytic Study of a Large Sample of Normal Elderly Volunteers," *Dementia,* vol. 5, pp. 266–281, 1994.

W.K. Anger, et al., "Symposium on Computerized Behavioral Testing of Humans in Neurotoxicology Research: Overview of the Proceedings," *Neurotoxicology and Teratology,* vol. 18, No. 4, pp. 347–350, 1996.

Cognitive Diagnostics, Inc., Website, www.brain.com, Apr. 26, 1999.

S.L. Miller et al., "Methods and Apparatus for Dynamically Tailoring Biochemical Based Therapy Programs in Human", U.S. patent application Ser. No. 09/100,663, filed Jun. 18, 1998.

* cited by examiner

| Test Subject | Test Subject Demographic Information | Initial Testing ||||  Perceptual Testing ||||
|---|---|---|---|---|---|---|---|---|---|
| | | 1 | 2 | ... | M | 1 | 2 | ... | N |
| A | | | | | 510 | | | | 514 |
| B | | | | | | | | | |
| ⋮ | | | | | | | | | |
| | | | | | | | | | |
| | | | | | | | | | |

FIG. 5

REMOTE COMPUTER-IMPLEMENTED METHODS FOR COGNITIVE AND PERCEPTUAL TESTING

This application is a continuation-in-part of a U.S. Patent Application entitled "Remote Computer-implemented Methods for Cognitive Testing" by Barbara Calhous et al., filed on Jan. 29, 1999 (U.S. Application No. 09/241,362), now U.S. Pat. No. 6,280,198 which is incorporated by reference herein.

BACKGROUND OF THE INVENTION

The present invention relates generally to techniques for cognitive and/or perceptual testing. More particularly, the present invention relates to remote computer-implemented methods for cognitive and/or perceptual testing to aid in assessing changes in a person's cognitive and perceptual status and building a testing database including the testing information.

Generally speaking, a cognitive skill may be defined as a decision that takes time to process. There are different components of cognitive skills including, for example, short term and long term memory, planning/prediction, set switching, speed, and spatial orientation. Cognitive testing is well established and there exists an abundant number of cognitive tests that measure different cognitive skills. Conventionally, the testing of cognitive skills consists of a battery of tests. For example, an IQ test can be part of cognitive testing.

A perceptual ability may be defined as a function performed by a primary sensory system. The primary sensory systems include the visual system, auditory system, somatosensory system, etc., and the function typically includes translating information from the external environment to an internal representation thereof. Similarly, perceptual testing is well established and there exists an abundant number of perceptual tests that measure different perceptual abilities. By way of example, auditory threshold tests may be used to measure a person's hearing threshold over a wide range of frequencies to assess the person's hearing abilities.

For a potential monitoring program, for example, monitoring a person at risk for a disorder (e.g., depression) that affects cognition and perception, evaluation of the person's cognitive skill levels and/or perceptual abilities may be desirable. The evaluation may also be desirable for monitoring a person using a biochemical based therapy, behavioral therapy, or any other therapy, where hundreds of different alternatives may be selected from. The evaluation may detect subtle changes in a person's cognitive skill levels and/or perceptual abilities. These changes in the person's cognitive and/or perceptual status may predict an impending change in the person's condition or an impending change in undesirable side effects from their therapy, and allow timely intervention.

In addition, it is often desirable to administer a particular therapy program that has the least undesirable side effects or to intervene with an ongoing therapy in case of the imminent occurrence of an acute crisis in a previously static situation. As different therapy programs may have different effects on specific cognitive skills and/or perceptual abilities, it is desirable to determine which cognitive skills and/or perceptual abilities, and to what extent these skills and/or abilities, are affected by a particular therapy alternative. Based upon this determination, a therapy program may then be elected which may fit the person's needs best, or a therapy program may be elected to intervene in a previously static condition.

One possible method for measuring a person's cognitive and/or perceptual status is through cognitive and/or perceptual testing. For example, for a person undergoing a new therapy program, cognitive and/or perceptual testing may allow monitoring and potentially useful feedback of either program efficacy or the presence of side effects due to the therapy.

In the past, cognitive and/or perceptual testing motivated by therapy programs has been limited to low frequency testing such as manual testing. The manual testing usually consists of face-to-face testing in a testing site such as a physician's office, for example. The testing frequency is then governed by the convenience or ability of the person to travel to the testing site. In another costly example, the person may remain in a hospital for high frequency testing of cognitive and/or perceptual status. However, the dramatic costs of inpatient health care may make this alternative prohibitively expensive. For these reasons, cognitive and/or perceptual testing frequency was usually limited to one test before treatment inception and one test once again several weeks to months afterwards.

Aside from the traditional face-to-face testing, there are current techniques that use computer-implemented methods for cognitive testing. The Neurobehavioral Evaluation System (NES2) as described by Baker et al. of Atlanta, Ga. is a computer-implemented method for testing cognitive skills on a low frequency basis. The testing is administered at a testing site and testing frequency is again limited by the person's ability to travel to the testing site. Thus, for assessing the effects of a therapy program for example, one disadvantage to the NES2 method is that practical considerations of administering the test at a testing site do not allow for monitoring the affects of the therapy program on a frequent basis.

Current cognitive and perceptual testing methods do not facilitate high frequency cognitive skill and perceptual ability assessment. For the case when monitoring of the cognitive skills and perceptual abilities is required on a daily basis, testing at a testing site is undesirable since it requires an inconvenient amount of travel for the person. In addition, practical considerations may also limit the frequency of testing when the time to travel to the testing center is longer than the testing duration. A further disadvantage of testing cognitive and perceptual status at a testing site, for example, for cases of chronic biochemical-based therapy (such as asthma medication) is the potential undesirable side effects (i.e. drowsiness) of the therapy, which may affect the person's ability to travel to the testing site.

In view of the foregoing, there are desired improved techniques for admministering and monitoring high-frequency cognitive and/or perceptual testing in a convenient and cost-effective manner.

SUMMARY OF THE INVENTION

To achieve the foregoing, the present invention relates to a computer-implemented methods and apparatus for remote cognitive and/or perceptual testing using a computer network having a remote computer geographically separate from an administering computer. The remote cognitive and/or perceptual testing includes administering a set of cognitive and/or perceptual tests, obtaining a performance response of the person to the tests and uploading the testing information via the computer network. Parallel to the testing, a therapy may be administered. The method may also include monitoring the performance of the person on the tests. The computer-implemented method may additionally include administering a set of initial tests before therapy inception to assess a person's intrinsic cognitive skills and/or perceptual abilities. The results of the initial testing and testing during therapy may be entered into a database. The database may be built from the performance response of multiple people and may be useful in predicting efficacy of a proposed therapy.

In one aspect, cognitive and/or perceptual status may be assessed by a set of interactive computer-implemented exercises, tasks and tests. Typically, the set of interactive exercises, tasks and tests provide an indication of one or more of the individual's cognitive skills and/or perceptual abilities. The tests may be administered a number of times effective to evaluate the cognitive skill levels and/or perceptual abilities. The testing is typically adaptive to maintain proximity to the subject's changing status as a result of a therapy program, for example. The adaptations in testing difficulty may be made according to previous response from the subject in one or more tests. Adapting the testing may include changing the tests, testing parameters, exercises and exercise stimuli. To facilitate a high level of engagement, computer-implemented animations and entertainment methods may be implemented in the exercises.

In one embodiment, the testing is applied before a therapy to get a pre-therapy indication of the individual's cognitive and/or perceptual status and after therapy inception to facilitate comparison. In another embodiment, testing is included regularly in a therapy program, e.g., on a daily basis or periodically during the therapy program. By allowing the subject to test at home, the present invention permits high frequency testing of cognitive skills and/or perceptual abilities. An advantage of the high frequency testing is improved resolution of cognitive and/or perceptual testing data and earlier feedback of therapy efficacy. Indeed, the high frequency testing may allow for detection of a subtle change in cognitive and/or perceptual status before the person is aware. The high frequency testing may also allow earlier intervention if necessary which may prevent long periods of exposure to negative side effects that would be felt if the testing was performed on an infrequent basis.

In one embodiment, the present invention relates to a computer-implemented method for remotely administering and monitoring cognitive and/or perceptual testing on a human subject, the method being implemented using a computer network having a monitoring computer and a remote administering computer, the remote administering computer being geographically remote from the monitoring computer and local to the human subject. The method comprising administering at least one of a cognitive and/or perceptual test to the human subject and obtaining a performance response of the human subject in the at least one of a cognitive and/or perceptual test. Administering and obtaining the at least one test are performed a number of times effective to evaluate at least one of a cognitive skill and a perceptual ability of the human subject. The method additionally includes uploading, testing information including the performance response from the administering computer via the computer network.

In another embodiment, the present invention relates to a computer-implemented method for remotely administering perceptual testing on a human subject, the method being implemented using a computer network having a monitoring computer and a remote administering computer, the remote administering computer being geographically remote from the monitoring computer and local to the human subject. The method comprising administering at least one perceptual test to the human subject and obtaining a performance response of the human subject in the at least one perceptual test using the remote administering computer. Administering and obtaining the at least one test are performed a number of times effective to evaluate at least one perceptual ability of the human subject. The method also includes uploading testing information pertaining to the performance response from the administering computer via the computer network.

Embodiments of the present invention also relate to mechanisms for storing and delivering computer readable instructions for remotely administering cognitive and/or perceptual tests for a person. Delivering the computer readable instructions may be across a computer network having an administering computer and a geographically remote computer. Delivering the instructions may include transmission of signals representing instructions for administering a set of cognitive and/or perceptual tests, obtaining a performance response of the person to the tests and uploading the testing information via the computer network to the administering computer.

These and other advantages of the present invention will become apparent to those skilled in the art upon a reading of the following descriptions of the invention and a study of the figures.

BRIEF DESCRIPTION OF THE DRAWINGS

The present invention is illustrated by way of example, and not by way of limitation, in the figures of the accompanying drawings in which:

FIG. 5 illustrates a database for storing the results of the computer-implemented cognitive and/or perceptual testing method in accordance with a specific embodiment of the present invention.

DETAILED DESCRIPTION OF THE PREFERRED EMBODIMENTS

Figure 1A:
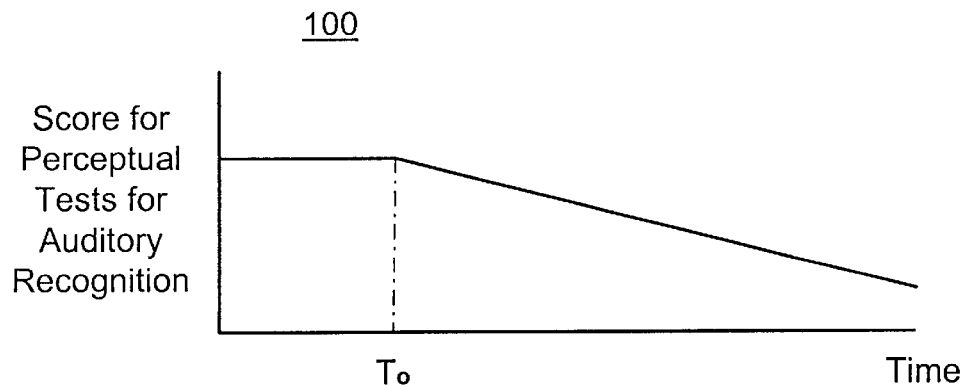
FIGS. 1A–C illustrate exemplary responses to testing of different cognitive skills and perceptual abilities before and after inception of a biochemical based therapy program, in accordance with some embodiments of the present invention.

The present invention will now be described in detail with reference to a few preferred embodiments thereof as illustrated in the accompanying drawings. In the following description, numerous specific details are set forth in order to provide a thorough understanding of the present invention. It will be apparent however, to one skilled in the art, that the present invention may be practiced without some or all of the specific details. In other instances, well known process steps and/or structures have not been described in detail in order not to unnecessarily obscure the present invention.

In accordance with one aspect of the present invention, there are provided methods and apparatus for remote computer-implemented testing of cognitive and/or perceptual status. By remote (i.e., local to the human subject) testing on a frequent basis, the practical inconveniences and potential inaccuracies of prior art testing techniques are advantageously avoided. Due to the convenience of the remote computer-implemented testing techniques, it may be possible to administer the testing in less time that it would take to travel to a testing center. In addition, the remote cognitive and/or perceptual testing on a high frequency basis may also allow for improved clarity of assessment by screening out random variation such as varying test times, fatigue due to travel, or mental factors involved in testing a person in an unfamiliar setting such as a hospital or an office. This type of cognitive and/or perceptual testing may be useful, for example, for companies and individuals looking to monitor the effects of biochemical based therapy on a person. In one embodiment of the present invention, a networked remote administration computer is used to administer the cognitive and/or perceptual testing.

Remote cognitive and/or perceptual testing may be useful for a potential therapy program where hundreds of different alternatives may be selected from and it may be desirable to administer the most effective therapy program with the least undesirable side effects. As certain particular therapy programs may affect separate cognitive skills and/or perceptual abilities, the goal then, in one embodiment of the present invention, is to determine which, and to what extent, cognitive skills and/or perceptual abilities are affected by a potential therapy program, and then elect a therapy program which fits the person's needs best.

As an example, in an epilepsy therapy program where a specific region of the brain may be targeted as the focal point of the hyperactivity problem, many anti-convulsant biochemical based therapy programs may be administered which target the desired focal point of the brain. On the other hand, it may be possible for these programs to undesirably affect other regions of the brain that are responsible for certain cognitive skills and/or perceptual abilities. Thus, the goal for finding a therapy program for epilepsy in this case may then be to find an alternative which affects the desired focal area of hyperactivity but does not unduly affect reaction time, balance, vision, coordination, or an ability to carry out daily activities such as driving or any other cognitive skills and/or perceptual abilities required for a normal lifestyle.

Thus, it may be advantageous to measure efficacy of a therapy program by measuring cognitive skills and/or perceptual abilities via cognitive and/or perceptual testing at a high frequency. The cognitive and/or perceptual status may be monitored for a period of time before and after inception of a particular therapy program and may be used to compare personal performance with and without the effect of the therapy. Further advantages of high frequency cognitive and/or perceptual testing may include higher resolution of cognitive skill and/or perceptual ability data and earlier feedback of effects of the therapy program. The high frequency testing also allows for noise or random inputs in the testing to be filtered out, which may provide a more accurate measure of the person's cognitive and/or perceptual status. This is advantageous over the prior art methods where discreet testing results are used to evaluate a human subject's performance during therapy, or are used to compare a subject's performance to discreet results from a large population.

In one embodiment of the present invention, prior to inception of a therapy program, a set of initial cognitive and/or perceptual tests may be administrated. In this manner, a reference performance of the human subject's cognitive and/or perceptual status may be established without the variable affect of any therapy. In a specific embodiment, initial testing is performed daily for one week prior to inception of a therapy program. Initial testing may also include testing the human subject's response to a large number of cognitive and/or perceptual tests in order to determine from the large number of tests which tests elicit a high level of engagement. As an example, five different cognitive tests and five different perceptual tests may be administered during initial testing, and three perceptual tests may be selected from these ten that may best maintain a high level of engagement for the individual. In one embodiment of the present invention, the initial cognitive testing is administrated using a remote computer.

After inception of the therapy program, the cognitive and/or perceptual testing is administered using the remote administration computer that is networked with the computer employed to monitor testing. In one embodiment of the present invention, the computer-implemented cognitive and/or perceptual testing may take the form of a set of exercises, tasks, tests or games that the human subject plays on the remote computer. By way of example, the computer-implemented cognitive and/or perceptual testing may take the form of two cognitive games and one perceptual game the person plays on a daily basis for twenty minutes. In some embodiments, the person may remain on substantially the same testing regimen (e.g., playing the games) at the same time every day after inception of the therapy.

The present invention includes a set of computer-implemented interactive exercises employed in a testing regime to periodically assess at least one of the subject's cognitive skill levels and/or perceptual abilities. The exercises include stimuli presented by a computer-based apparatus to engage one or more of a subject's cognitive skills and/or perceptual abilities. The stimuli may include visual, audio, tactile and somatosensory information, for example. In one embodiment, a testing regime requires the user to respond to the exercises. The subject's performance may be assessed, with or without the subject's awareness.

Figure 1B:
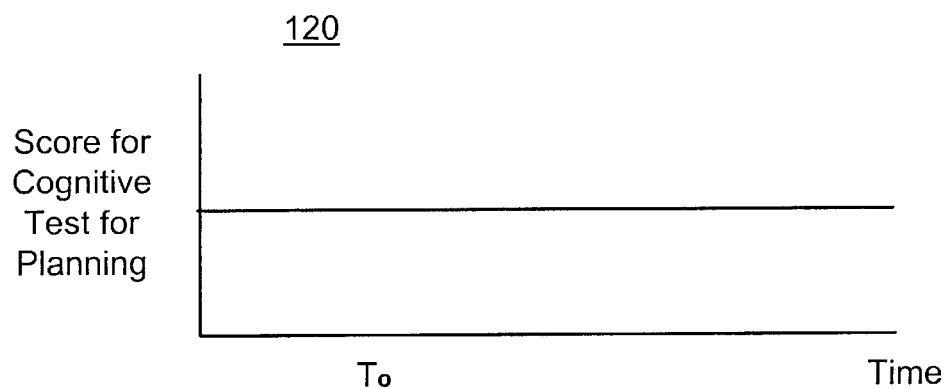
Figure 1C:
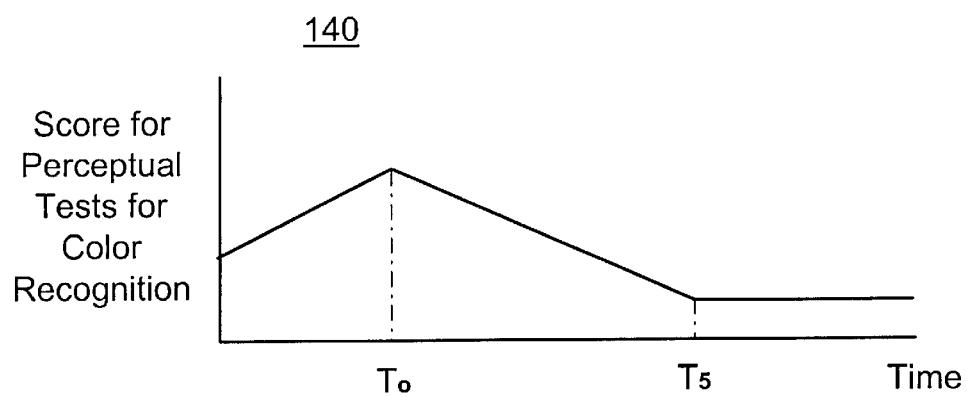

FIGS. 1A–1C illustrate examples of different responses to testing of various cognitive skills and/or perceptual abilities by a human subject. FIGS. 1A–1C illustrate that when therapy is administered to the subject, certain cognitive skills and/or perceptual abilities may be affected (as revealed by the tests) while others may not change.

FIG. 1A illustrates a performance 100 of a human subject for a set of perceptual tests which assess auditory recognition. In this case, the performance of the human subject remains constant during initial testing (testing prior to therapy inception time $T_0$) and decreases linearly after administration of a biochemical based therapy begun at inception time $T_0$.

FIG. 1B illustrates a performance 120 of a human subject for a set of cognitive tests which test for planning. In this case, the performance of the human subject does not change with time during initial testing and does not change over time with inception of a therapy begun at inception time $T_0$.

FIG. 1C illustrates a performance 140 of a human subject for a set of perceptual tests which test for color recognition. In this case, the performance of the human subject improves linearly over time during initial testing, diminished after inception of a therapy begun at inception time $T_0$, and remains constant after time $T_5$ during testing.

Having briefly discussed some general aspects and advantages of the present invention, the features and advantages of these aspects may be better understood with reference to the figures and discussions that follow. As mentioned earlier, the cognitive and/or perceptual testing techniques of the present invention are preferably implemented using a computer-based apparatus.

Figure 2:
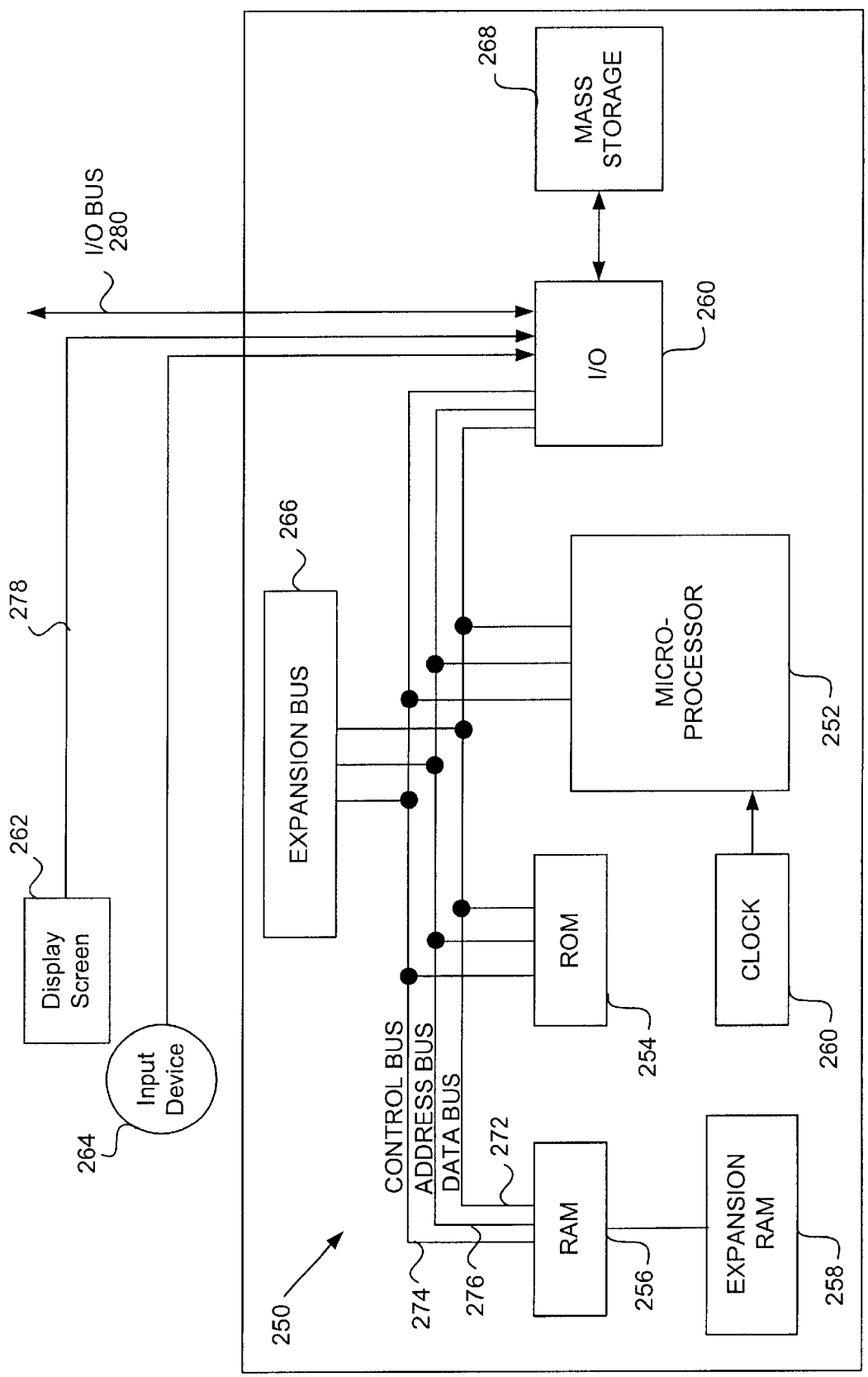
FIG. 2 illustrates a general-purpose computer system, representing a computer suitable for implementing the present remote cognitive and/or perceptual testing method.

FIG. 2 illustrates, in accordance with one embodiment of the invention, an exemplary computer-controlled apparatus, including a computer system 250, for delivering computer-controlled stimuli to test cognitive skills and/or perceptual abilities.

Referring to FIG. 2, the computer system 250 in accordance with the present invention includes a central processing unit (CPU) 252, read only memory (ROM) 254, random access memory (RAM) 256, expansion RAM 258, input/output (I/O) circuitry 260, display assembly 262, input device 264, and expansion bus 266. Computer system 250 may also optionally include a mass storage unit 268 such as a disk drive unit or nonvolatile memory such as flash memory and a real-time clock 260. In one embodiment, mass storage unit 268 may include units which utilize removable computer readable media, such as floppy disks, opto-magnetic media, optical media, and the like for the storage of programs and data.

CPU 252 is preferably a commercially available, microprocessor including a chip such as one of the Intel X86 or Motorola 680XX family of chips, a reduced instruction set computer (RISC) chip such as the PowerPC™ microprocessor available from Motorola, Inc, or any other suitable processor. CPU 252 is coupled to ROM 254 by a data bus 272, control bus 274, and address bus 276. ROM 254 may partially contain the basic operating system for the computer system 250. CPU 252 is also connected to RAM 256 by busses 272, 274, and 276 to permit the use of RAM 256 as scratch pad memory. Expansion RAM 258 is optionally coupled to RAM 256 for use by CPU 252. CPU 252 is also coupled to the I/O circuitry 260 by data bus 272, control bus 274, and address bus 276 to permit data transfers with peripheral devices.

I/O circuitry 260 typically includes a number of latches, registers and direct memory access (DMA) controllers. The purpose of I/O circuitry 260 is to provide an interface between CPU 252 and such peripheral devices as display assembly 262, input device 264, mass storage 268, headphones, speakers, sensors (e.g. force) and/or any other I/O devices. Display assembly 262 of computer system 250 is an output device for displaying objects and other visual representations of data.

The screen for display assembly 262 can be a device that uses a cathode-ray tube (CRT), liquid crystal display (LCD), or the like, of the types commercially available from a variety of manufacturers. Input device 264 can be a keyboard, a mouse, a stylus working in cooperation with a position-sensing display, or the like. Alternatively, input device 264 can be an embedded RF digitizer activated by an "active" RF stylus. As a further alternative, input device 264 may be any type of switches capable of communicating a user response to computer system 250. Therefore, as used herein, the term input device will refer to any mechanism or device for entering data and/or pointing to a particular location on a screen of a computer display. The aforementioned input devices are available from a variety of vendors and are well known in the art.

Some type of mass storage 268 is generally considered desirable. However, mass storage 268 can be eliminated by providing a sufficient amount of RAM 256 and expansion RAM 258 to store user application programs and data. In that case, RAMs 256 and 258 can optionally be provided with a backup battery to prevent the loss of data even when computer system 250 is turned off. However, it is generally desirable to have sonic type of long term mass storage 268 such as a commercially available hard disk drive, nonvolatile memory such as flash memory, battery backed RAM, PC-data cards, or the like.

In operation, computer system 250 is employed to generate stimuli of the various cognitive and/or perceptual tests. These stimuli may be furnished to the test subject using any of the output devices, including display assembly 262, headphones, speakers, or any other output device. Responses from the user may then be recorded by input device 264 or sensors in communication with I/O Bus 280 and analyzed by CPU 252. If desired, feedback to the user may be given at various stages of the test(s) via display assembly 262, headphones or speakers.

The computer system 250 is also employed to receive information related to various cognitive and/or perceptual testing from one or more sensors in communication with I/O circuitry 260 via I/O Bus 280 and (I/O) circuitry 260. The sensors may include of those used for obtaining feedback of a subject's performance in a visual, auditory and somatosensory test. For example, the sensors may be force sensors included in a tactile testing apparatus or force and velocity sensors included in a treadmill used for vestibular testing. The aforementioned sensors are available from a variety of vendors and are well known in the art.

It should be borne in mind that although computer system 250 is discussed in detail herein to facilitate discussion, the inventive cognitive testing technique may be practiced on a variety of suitable computer-implemented techniques. By way of example, the inventive remote cognitive testing technique disclosed herein may be implemented via a computer network, such as a local area network (LAN), wide area network (WAN) or a global computer network such as the Internet. In the latter case, the inventive remote cognitive testing technique may be implemented as downloadable computer software and data (e.g., applets). The downloadable computer software and data may be kept on one or more servers on the network, accessible by any client computer or terminal capable and authorized for such access. To facilitate testing, the downloadable computer software and data can be downloaded once and reused over and over at the client computer/terminal. Alternatively, the downloadable computer software and data can be downloaded for each individual testing session via the network as needed. Network computing techniques and implementations are well known in the art and therefor are not discussed in great detail here for brevity's sake.

In accordance with another aspect of the present invention, the remote cognitive and/or perceptual testing techniques are optimized for full computerized testing with minimal involvement by another person other than the test subject. That is, the testing may be designed to be generated by a computer or computer controlled apparatus for testing without continual external supervision. In one embodiment of the present invention, as long as the appropriate instructions are provided to the remote. testing computer, the entire testing can be performed by the test subject using a remote administration computer without involving supervisory assistance. In this manner, testing can be administered with a high degree of convenience and at a relatively low cost. Additionally, cognitive and/or perceptual discrepancy detection in the subject's responses may be designed such that they do not require intervention or supervision by a trained person who administers the tests. In a specific embodiment, the cognitive and/or perceptual testing data is transmitted to the remote administration computer by the monitoring computer. The testing performance and data may then be returned from the remote computer to the monitoring computer and used as appropriate (e.g., for analysis).

Having briefly discussed the remote computer-implemented methods of the present invention, some exemplary cognitive and/or perceptual tests will be now be discussed.

Generally speaking, a cognitive test is a test in which at least one cognitive process is relevant to the subject's performance in the test. Cognitive tests and skills may include those described above as well as those which utilize any other cognitive processes known in the art. In some embodiments of the present invention, a cognitive process may involve a manipulation of the internal representation of the information provided in a task.

A perceptual test is a test in which a function performed by a primary sensory system is relevant to the subject's performance in the test. By way of example, a test may include inputting (to the computer) whether the subject perceived a sound provided by the computer. Typically, cognitive processes are not relevant to the subject's performance in a perceptual test. It should be noted that the perceptual test may include cognitive performance in executing the perceptual test. For example, cognitive processing may be used in understanding the instructions of the test.

It is important to note that cognitive and/or perceptual testing are well established in the art. Thus, there are numerous cognitive and/or perceptual exercises and tests that may used by the remote computer-implemented testing methods of the present invention. Factors which may affect which tests are chosen include results obtained during initial testing, prior performance of a particular cognitive and/or perceptual test for a therapy, prior performance of a test in a particular demographic group, etc.

An exercise may test for more than one cognitive skill and/or more than one perceptual ability. As an example, one type of cognitive exercise used in the proposed remote computer-implemented method is a maze-type game. The configuration of the maze-type game allows the rules to be changed such that the test may probe different cognitive skills. For example, a maze may be used that has many starting points and a single exit. If the test rules are designed such that the person is penalized for entering and not successfully exiting, then the game may test the person's ability to plan. A further example is if the rules of the maze game are altered. For example, if input from the human subject is reversed such that right becomes left, and left becomes right, the game may test for a person's ability to adapt to rule changes or the cognitive skill of switching. Cognitive skills can also be measured by the person's ability to solve a problem, cope with switching rules or finish in a timely manner.

Figure 3A:
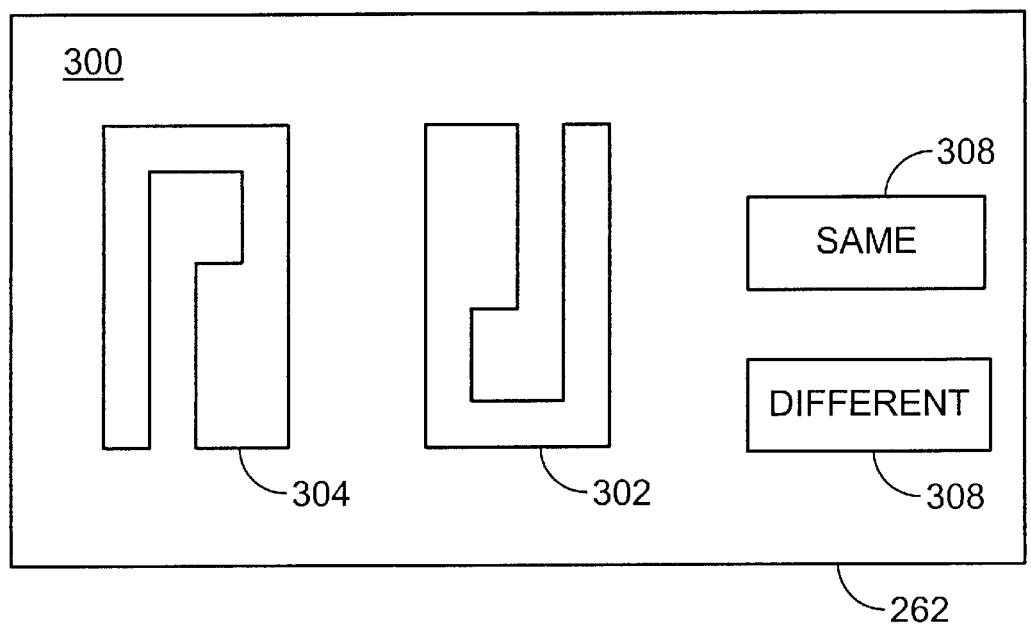
FIG. 3A illustrates a block exercise which may be used to test cognitive and/or perceptual status in accordance with one embodiment of the present invention.

FIG. 3A illustrates a block exercise 300 in accordance with one embodiment of the present invention. The block exercise 300 may be used to present a cognitive test and a perceptual test. The block exercise 300 includes two block structures 302 and 304. In one suitable cognitive test using the block exercise 300, the subject is required to respond if the block structures 302 and 304 are the same or different in shape. More specifically, after display of the block structures 302 and 304 on the display screen 262, the subject is required to input to the computer using answer blocks 308 whether the block structures 302 and 304 are the same or different in shape. The cognitive process required in this case include manipulating orientation of the internal representations of the block structures 302 and 304.

The block exercise 300 may also be used to test a perceptual ability. In one suitable perceptual test using the block exercise 300, the block structures 302 and 304 are displayed on the display screen 262 having different colors and the subject is required to respond if the block structures 302 and 304 are the same color. In this case, the perceptual ability required to execute the block exercise 300 is visual color detection.

The present invention may also implement auditory perceptual and cognitive tests. In one suitable auditory perception test, a subject is provided with two tonal stimuli and is required to input to the computer whether the tonal stimuli are the same. The two tonal stimuli may differ in frequency and duration, for example. Thus, in the perceptual test, cognitive processing may be used in executing the instructions of the task, e.g. as clicking an appropriate box on the screen, however, the performance in the test is dependent upon an auditory ability and is not related to the cognitive skill in executing the test. In one suitable cognitive test using the same two tonal stimuli, a subject is provided with the two tonal stimuli multiple times in a series and then is required to reconstruct the series to the computer using appropriate GUI boxes and a mouse.

Other exercises suitable for use with the present invention include the presentation of numbers and letters. These exercises including the presentation of numbers and letters may be used to provide cognitive tests and perceptual tests. In one suitable cognitive test using numbers, the subject is provided a series of numbers and is required to input the series of numbers back to the computer in the reverse order. The series of numbers may be provided auditorally or visually, for example.

Exercises involving letters may include the use of one or more colors. A suitable cognitive test using colored letters includes presenting a series of letters such that multiple colors are presented and prompting the subject to perform a suitable task. By way of example, half the letters may be black and the other half of the letters red and the subject is required to determine if a red letter 'w' is present.

The exercises using the series of numbers and letters may also be used for perceptual tests. In one embodiment of the present invention, 'pop-out' tests are used to test perceptual abilities. A 'pop-out' test is one in which the information does not have to be scanned to execute the test. One suitable pop-out test for use with the present invention includes the presentation of letters in one or more colors. A suitable perception test includes presenting a series of letters such that one letter in the series may have a second color separate from the other letters. The subject is then required to input if a second color is present. By way of example, nine letters may be blue and one letter green and the subject is required to input if a green letter is present.

In accordance with another embodiment of the present invention, perceptual testing includes backward masking. Backward masking typically includes the presentation of a stimulus followed by noise. A test including backward masking requires the human subject to respond if they perceived the stimulus. Backward masking may be used to test any of the auditory, visual and somatosensory systems.

Figure 3B:
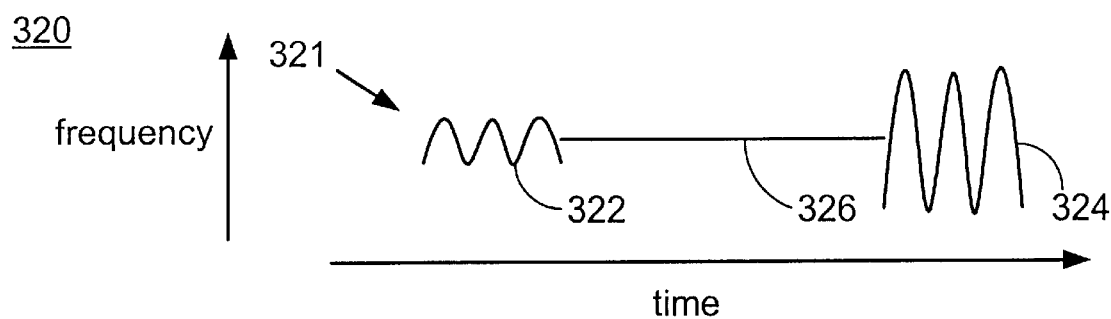
FIG. 3B illustrates an auditory backward masking test in accordance with a specific embodiment of the present invention.
Figure 3B:
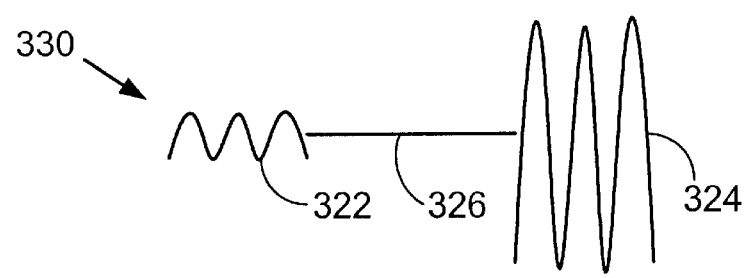

FIG. 3B illustrates an auditory backward masking test 320 in accordance with a specific embodiment of the present invention. The backward masking test 320 includes a test auditory stimulus 321 comprising a tonal stimulus 322 followed by noise 324 and separated by a delay 326. The backward masking test 320 requires the human subject to respond if they perceive the tonal stimulus 322.

The testing is typically adaptive. As therapy proceeds and perceptual and/or cognitive status changes, the testing may adapt to maintain proximity to the subject's changing status. The adaptations in testing difficulty may be made according to previous response from the subject in one or more tests. Adapting the testing may include changing the tests, testing parameters, exercises and exercise stimuli. By way of example, different tests may be introduced to assess a cognitive skill or perceptual ability as testing proceeds. In some cases, the different tests selected may be based on previous performance of the subject in the testing. Alternatively, the testing parameters and exercise stimuli may be modified to vary testing difficulty. The modifications may include changes in temporal, intensity and spatial parameters of the stimuli, for example.

The backward masking test 320 may be used to briefly illustrate some adaptive features of the present invention. To vary difficulty of the backward masking test 320 according to changing perception levels in a human subject during a therapy, the parameters of the backward masking test 320 may be altered. By way of example, the duration of presentation of the stimulus 322 and the noise 324 may be altered. To decrease difficulty in the backward masking test 320 (e.g., according to decreasing auditory perception as a result of a therapy), the duration of presentation of the stimulus 322 may be increased or the duration of presentation of the noise 324 may be decreased. Alternatively, the delay 326 may be decreased in duration to increase testing difficulty for the backward masking test 320. The adaptations to the stimulus 322, the noise 324 or the delay 326 duration may be made according to a previous response from the subject in the backward masking test 320. Difficulty for the backward masking test 320 may also be changed by adapting the intensity and bandwidth of the stimulus 322 and the noise 324. By way of example, a test auditory stimulus 330 includes a shorter delay 326 and a larger bandwidth for the noise 324 relative to the test auditory stimulus 321 to increase testing difficulty for the backward masking test 320.

In one embodiment, a quantitative mechanism may be implemented to aid in assessment of the subject's responses as well as to aid in adapting the tests. The quantitative mechanism may be based on numerical representation and assignment of the testing parameters. The representation and assignment may include a formula comprised of a number of variables and weights which represent the stimuli and modification to the stimuli. By way of example, weights may be given to the intensity and duration of the stimulus 322, the noise 324 and the delay 326 in the backward masking test 320. The quantitative assessment mechanism may be expressed as any arbitrary Boolean equation or any other logical expression, relation or mathematical representation. As an alternate example, the complexity of mazes used in cognitive planning tests may be given numerical representation. In this manner, exercise designers may designate a quantitative mechanism for assessing difficulty of a test and performance of the subject in the test. The quantitative assessment mechanism may then be used between exercises to compare performance of the individual. Typically, a quantitative assessment of the individual's performance would drive alteration to the testing parameters between tests. The quantitative assessment mechanism may also be used to determine if new tests are to be used. In addition, the subject's performance using the quantitative assessment mechanism may then be tracked as testing progresses to produce scores such as those as illustrated in FIGS. 1A–C.

Typically, different cognitive skills have varying reactions to a therapy. In addition, different perceptual abilities have varying reactions to a therapy. These varying reactions allow flexible selection of what cognitive skills and/or perceptual abilities are used to monitor for therapy efficacy or side effects associated with the therapy.

Further, the reaction of a particular perceptual ability and a cognitive skill which requires use of the particular perceptual ability may vary in response to a therapy. By way of example, for a biochemical based therapy for depression, visual contrast sensitivity (a perceptual ability) may diminish at different rates with a therapy administration than cognitive skills which require visual contrast sensitivity. Generally speaking, perceptual abilities are less sensitive to a therapy than cognitive skills. In other words, cognitive skills typically tend to be disrupted by a therapy program more than perceptual abilities. Knowledge of these varying reactions may also be used for flexible selection of what cognitive skills and/or perceptual tests are administered to monitor for therapy efficacy or side effects associated with the therapy.

In one embodiment of the proposed invention, the tests used in the remote computer-implemented cognitive testing method orthogonally test for different components of cognitive skills. In this manner, isolation of the different cognitive skills may be achieved. As an example, three tests of cognitive skills may be provided, one which may test for short-term memory, the second which may test for switching (the ability to adapt to the rules of a cognitive test or game), and the third may test for spatial orientation.

The novel concept of remote cognitive and/or perceptual testing may also introduce new demands addressed by the present invention. For cognitive and/or perceptual tests administered at a high frequency, it is desirable for testing to be administered in a manner to engage the person sufficiently. For example, it is desirable for testing to be administered in a manner in which the person's intensity and focus is not diminished over the testing session. Thus, it may be desirable for the testing method and tests chosen prior to testing, or selected during initial testing, to be sensitive to the human subject's personal engagement levels.

To facilitate a high level of engagement, computer-implemented animations and entertainment methods may be implemented in the exercises. In one embodiment, the tests are disguised in a computer game. By way of example, the well known game Tetris may be used as a cognitive test associated with a high level of engagement for testing the cognitive skills of spatial orientation and reaction time. Alternatively, animations may be used, for example, in the reward of correct responses. Further, the testing may also include rewards for correct responses and a substantial amount of surprise to maintain interest by the subject. Thus, the testing exercises may be selected for their ability to engage the individual's intense, test-by-test attentional focus while at the same time ensuring that the individual is substantially rewarded for correct and near correct responses.

Figure 4A:
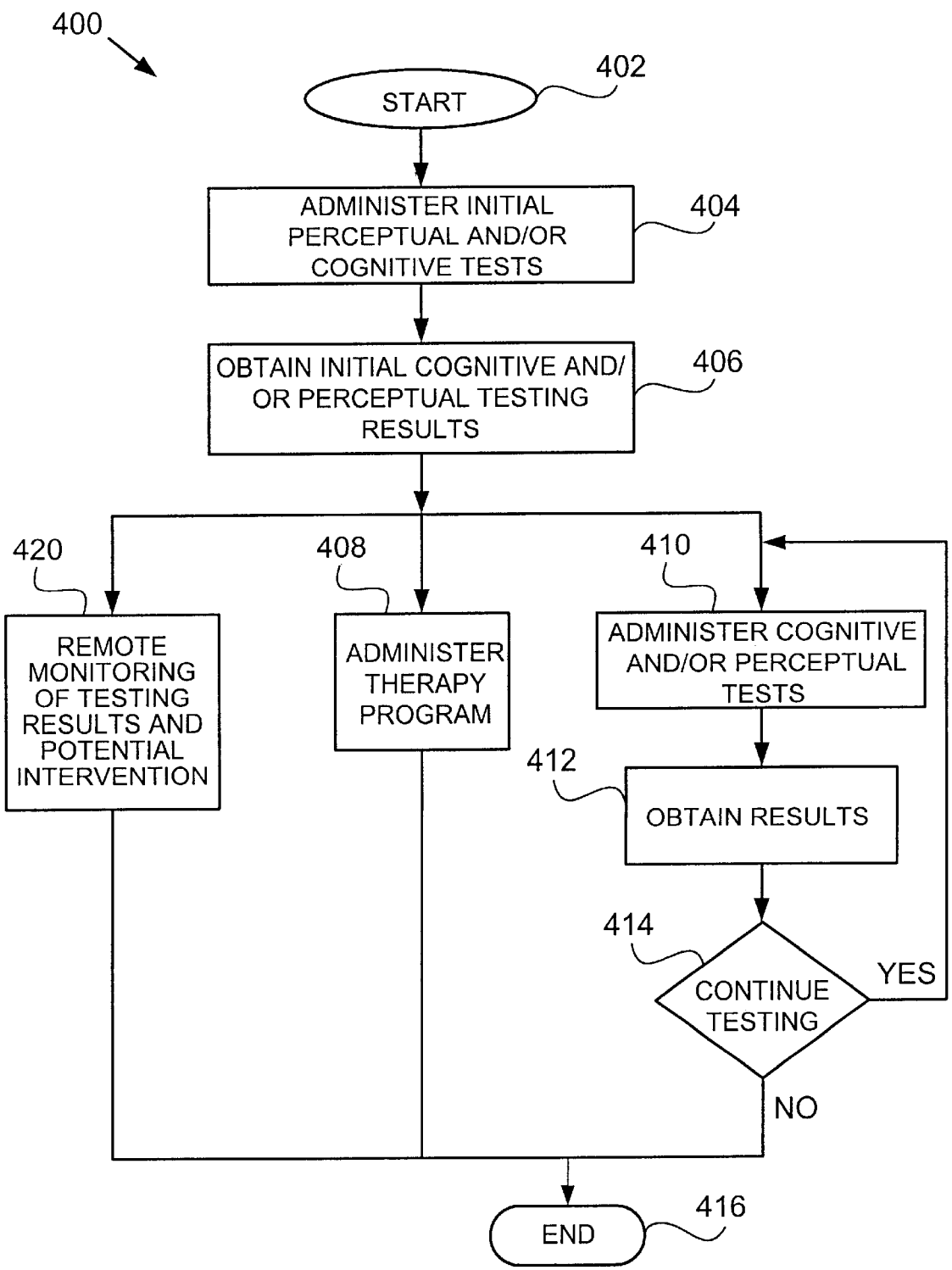
FIG. 4A illustrates the computer-implemented technique for initial testing and remote testing of cognitive and/or perceptual status before and after inception of a therapy program in accordance with one aspect of the present invention.

FIG. 4A provides a flowchart 400 for a method of administering cognitive and/or perceptual testing in accordance with one embodiment of the present invention. Processes in accordance with the present invention may include up to several additional steps not described or illustrated here in order not to obscure the present invention.

The flowchart 400 starts with administering a set of initial tests to obtain an intrinsic perceptual and/or cognitive status for the human subject (404). These tests may be administered at an administration site or preferably using a remote administration computer. Prior to testing in the flowchart 400, appropriate tests for the human subject may be selected based on, for example, demographics and the proposed therapy program. The flowchart 400 illustrates the testing procedure for testing multiple perceptual abilities once the appropriate tests are determined. It is understood that any number of other cognitive skills and/or perceptual abilities may be additionally added to or removed from the testing and that the testing for the flowchart 400 may vary for different cognitive skills and/or perceptual abilities. Initial intrinsic abilities and data may be obtained from the person (406). For the case where testing is done on a remote administration computer at home away from an administration and monitoring site, obtaining the initial data from the person may involve transmitting data from the remote computer onto a server at the monitoring site.

Preferably, the initial testing is performed at the same time and in the same location as subsequent testing after inception of the therapy. Thus, as mentioned before, a novel advantage of the proposed invention is the person's ability to test at home at convenient times which may improve clarity of testing assessment. This hopefully minimizes random variation prevalent in the prior art for testing at an administration site such as varying test times, fatigue due to travel, or mental factors involved in testing a person in an unfamiliar setting such as a hospital or an office.

The therapy program is then administered (408). Therapy administration (408), testing (410) and monitoring (420) may be performed concurrently. Typically, when the therapy program begins, the cognitive and/or perceptual testing begins (410) to measure the efficacy and/or side effects of the therapy on the particular cognitive skills and/ or perceptual abilities being tested. The therapy program may be administered for a predetermined time or the therapy program duration may be flexibly administered. It should be borne in mind that perceptual and/or cognitive testing may be administered for a longer or shorter period of time than the duration of the therapy program. For example, testing may also continue after therapy has ended for purposes of data collection and building a database. In one embodiment of the present invention, the duration of perceptual and/or cognitive testing may be determined by the efficacy of the therapy program in terms of degradation of a particular perceptual ability and/or cognitive skill.

The testing data and the testing results are transmitted to the administration site server (412). The administration site server may further transmit the data to a monitoring computer or may transfer the data to a database which stores all the testing results, permitting an administrator to monitor the person's performance infrequently over time. Remote monitoring (420) includes monitoring testing results to determine if intervention is necessary, and to intervene, if necessary. For example, if significant changes in perceptual and/or cognitive status are being observed, intervention of the therapy program being administered or the tests being administered may be necessary.

The person responsible for the remote monitoring may also be responsible for determining whether testing will continue (414). Alternatively, a predetermined criteria can be used to determine whether testing will continue, e.g. maintaining a predetermined threshold for performance in the tests based on a quantitative mechanism. If there is no significant changes in performance of perceptual and cognitive skills due to the therapy, then testing may be ended. Further, remote monitoring may also include assessing the appropriateness of the therapy program. Remote monitoring (420) also monitors the efficacy of the therapy program for side effects.

Thus, in the flowchart 400, the number of times that testing may be administered is flexible and may be based on numerous criteria. In some embodiments of the present invention, testing is repeatedly administered and results are repeatedly obtained for a number of times effective to evaluate the cognitive and/or perceptual status for the human subject. In a specific embodiment, testing is administered and results are obtained once to evaluate the cognitive skill and/or perceptual ability of said human subject. Of course, the number of times that the testing is administered may also be effected by the tests used, the individual, and the motivation for testing.

Although the flowchart 400 illustrates one embodiment which includes administering a set of cognitive and/or perceptual initial tests in addition to a set of cognitive and/or perceptual tests during a therapy, the present invention is not limited to including initial testing or testing during administration of a therapy. By way of example, the present invention may include testing cognitive skills and/or perceptual abilities with administration of a therapy without testing for initial status. In addition, the present invention may include testing cognitive skills and/or perceptual abilities without administration of a therapy and without including initial testing.

In accordance with one embodiment of the present invention, the high frequency testing of the flowchart 400 represents remote cognitive and/or perceptual testing on a daily basis. In another embodiment of the present invention, the high frequency testing represents remote testing twice a week. In accordance with yet another embodiment of the present invention, testing is administered multiple times per day. As can be appreciated by those skilled in the art, such frequent cognitive and/or perceptual testing would have been prohibitively expensive if performed in accordance with prior art techniques which often require inpatient care at a medical facility.

As there is no current technique for convenient, cost-effective high frequency testing of cognitive and/or perceptual status, there is no means for collecting results based on high frequency testing. Collection of high frequency cognitive and/or perceptual testing results may also permit the potential to build a database that contains testing information for a large number of people. This information may then be useful in future assessment and election of proposed therapy programs.

The database may be useful in measuring the side effects a therapy program may have on one or more cognitive skills and/or perceptual abilities. In addition, the database may also be useful in selecting a therapy program based on the prior response of numerous people to previous similar therapy programs. Alternatively, the database may also be useful in assessing a person's progress with respect to previous cases. For example, if in previous testing for a particular perceptual ability and therapy, the ability is consistently linearly improved over time for hundreds of subjects, these results may be compared against the current performance of a human subject for the same therapy program to determine whether the human subject is responding as expected. In this manner, the database may flexibly be used to aid in monitoring and assessment of therapy efficacy by detecting discrepancies in cognitive and/or perceptual ability trends.

Although response to a therapy program may vary from person to person, there may be trends in response to a therapy program that are common for a demographic group. It is then desirable, in one embodiment of the present invention, to test the response of a human subject to a therapy program according to their specific demographic group status. In this manner, the efficacy of the therapy program for a large number of people belonging to that demographic group may be monitored and assessed. In a further embodiment of the present invention, the database may be used to predict potential suitability of therapy programs or aid in selecting a therapy program which fits a person's needs based on their demographic status.

One advantage of building a database is that general improvements of a large number of human subjects may be used to correlate an expected improvement for a person belonging to a particular demographic group. This general trend extrapolated from the database information may then be used in future administration to help predict and interpret the response of a therapy program. In other words, if the human subject does not produce an expected result in comparison to the trends stored in the database for a large number of people in his demographic group, the database information may be used to signal a potential discrepancy for the human subject.

Figure 4B:
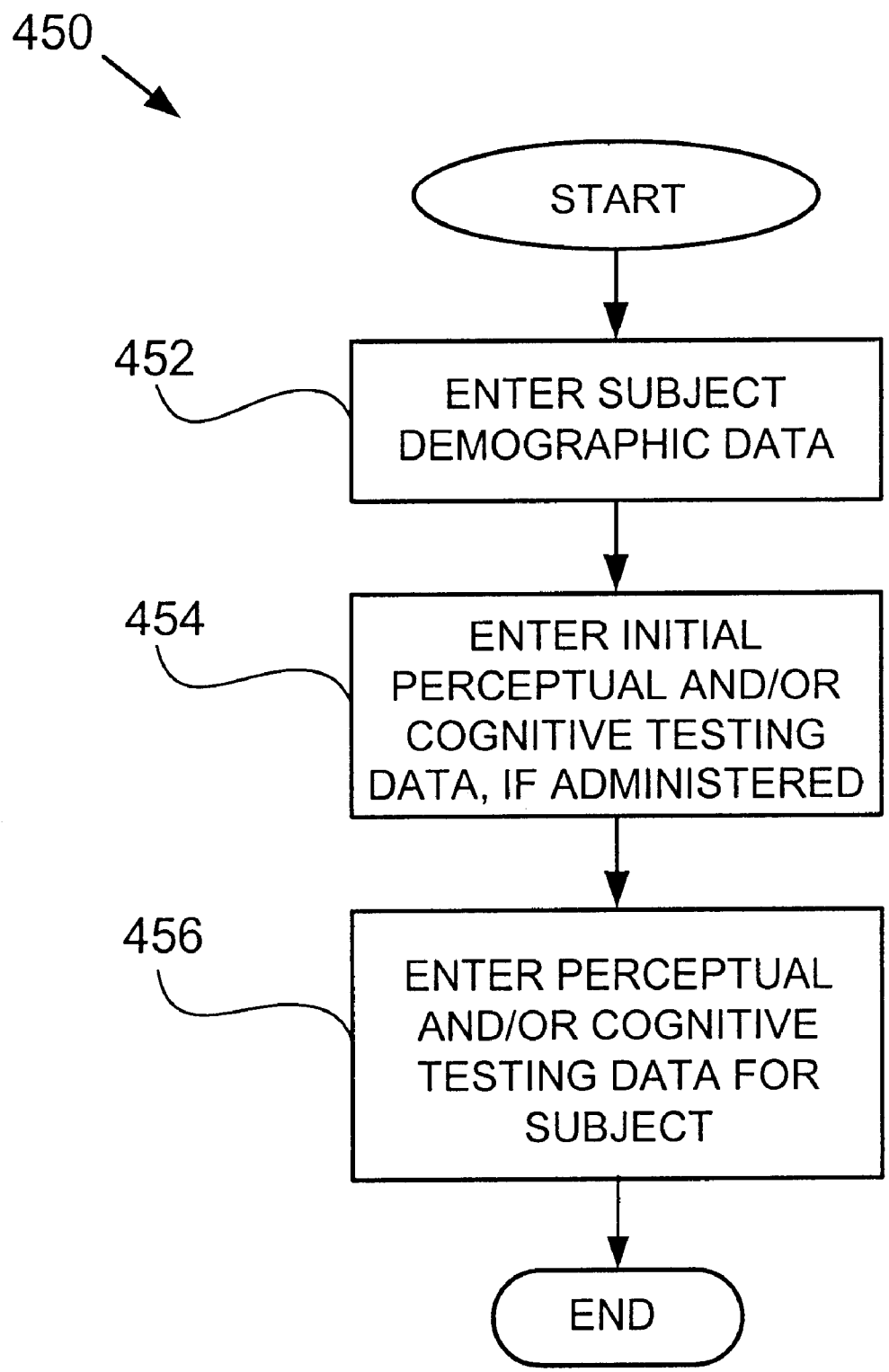
FIG. 4B illustrates the remote computer-implemented technique of building a database in accordance with one embodiment of the present invention.

FIG. 4B provides a flowchart 450 for a method of building a database including cognitive and/or perceptual testing information in accordance with one embodiment of the present invention. Processes in accordance with the present invention may include up to several additional steps not described or illustrated here in order not to obscure the present invention.

The flowchart 450 starts with a user initiating a file for a subject. Opening a file may include identifying the subject and entering demographic data for the subject (452). The data obtained during initial testing (406 of FIG. 4A) is entered into the database (454). The remote computer-implemented test results obtained from the subject are also entered for test subject (412 from FIG. 4A). In one embodiment, entering the initial testing data (454) and the testing data after therapy inception (456) into the database may be performed for each day of testing.

Information stored in a database in accordance with the present invention may also be made available to individuals other than those who maintain and monitor the database. By way of example, cognitive and/or perceptual testing data, initial testing data, and other information (e.g., expected results for a set of tests) stored in a database may be provided to individuals who are permitted access from a computer geographically separated from the computer having the database. In a specific embodiment, information stored in a database is provided to a subject who performed prior testing related to testing information in the database. In some cases, the person may use this information from the database for the purposes of self-evaluation, e.g., with respect to a health issue. The subject may gain access to the database via the Internet, for example, and may be use any access protocol known in the art which may limit or determine what information may be attained from the database.

Figure 5:
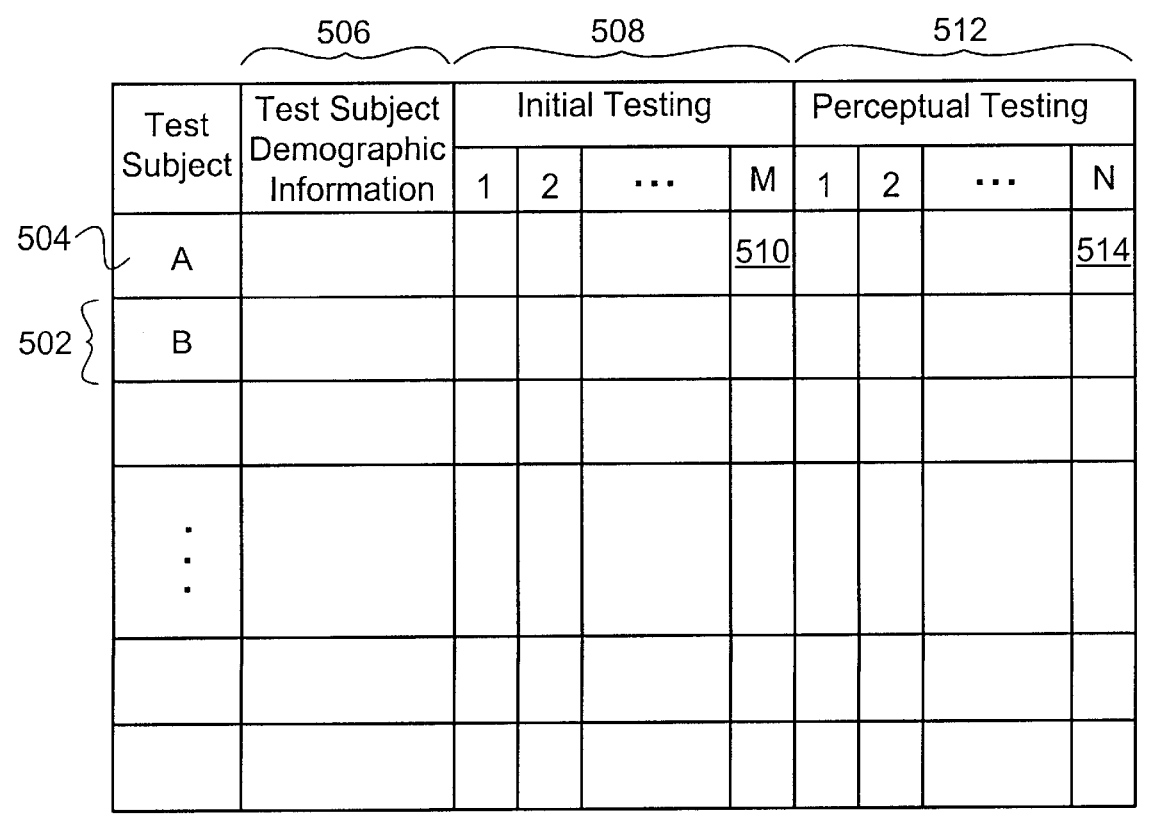

FIG. 5 illustrates a database 500 used for storing the perceptual testing results of a particular perception ability in accordance with one embodiment of the present invention. The perception ability stored in the database 500 includes responses to testing the ability during application of a therapy program for a large number of people. An entry 502 is designated for storing information pertaining to a single person in a single training session, such as testing according to FIG. 4. The entry 502 includes a portion 504 for storing data for identifying the human subject. A demographic portion 506 stores information related to the subject's demographic data, e.g. name, age, sex, etc. An initial testing portion 508 includes information obtained during initial testing (e.g., 406 of FIG. 4A). The initial portion 508 may be further divided into (M) daily sections 510. Similarly, a perceptual testing portion 512 includes information obtained during perceptual testing (e.g., 412 of FIG. 4A) and is divided into (N) daily sections 514. The number of days of initial testing (M) and the number of days of remote perceptual testing (N) are flexibly determined and may change from person to person and entry to entry.

In one embodiment of the present invention, the database 500 may be separated by demographic status. For example, all cognitive and/or perceptual testing responses corresponding to a specific age bracket and sex may be grouped. The information in the database 500 may further be supplied from the first monitoring computer to a second monitoring computer for additional monitoring by alternate parties. This may allow multiple administrators and clinicians to monitor the results of a single human subject.

In some embodiments where database 500 is implemented for one cognitive skill or perceptual ability and one therapy program among many people, it is common for a person to be entered in numerous databases for different cognitive skills and/or perceptual abilities and different therapy programs. In addition, a person may have multiple entries in the database 500 pertaining to multiple testing sessions over different periods of time. Database 500 composition and structure may vary widely as is well known in the art and alternatives are not included for brevity's sake.

Another advantage of high frequency testing is improved resolution of cognitive and/or perceptual testing data and earlier feedback of therapy efficacy. Indeed, the high frequency testing may allow for detection of a subtle change in cognitive and/or perceptual abilities before the person is aware. The high frequency testing may also allow earlier intervention if necessary which may prevent long periods of exposure to negative side effects that would be felt if the testing was performed on an infrequent basis. Thus, detecting the early warning signs of the side effects of a therapy program before they evolve into a major problem is now possible with the proposed invention. For example, in an AIDS therapy program, the high resolution of the proposed computer-implemented cognitive and/or perceptual testing method may be used to detect the early signs of dementia long before actual onset of the problem due to prolonged exposure to the therapy program.

The high frequency testing may also allow for noise or random inputs into the testing to be filtered out, which may lead to a more accurate measure of the person's cognitive and/or perceptual abilities. For example, in the case of low frequency testing, infrequent factors such as having a bad day may largely affect the results of cognitive and/or perceptual testing.

A further advantage of the novel remote computer-implemented cognitive and/or perceptual testing is that a person may be tested in a familiar environment that may not introduce stresses or testing disturbances that a foreign test center may introduce. For example, in the testing of high blood pressure, it is common that the testing center itself and the travel to the testing center causes stresses that bias the high blood pressure tests. Alternatively, testing in a comfortable home setting may remove some uncontrollable testing variables which may improve cognitive and/or perceptual testing control. Similarly, cognitive and/or perceptual tests can be affected by unfamiliar settings or distractions. The proposed remote testing method may also allow for cognitive and/or perceptual testing to be repetitively taken at the same time each day, allowing for improved clarity of the testing.

In one embodiment, the computer-implemented methods allow treatment to be remotely performed at home, thus providing convenience and facilitating flexibility in the training. The proposed invention also covers computer readable medium that includes instructions for testing as described above. More specifically, the present invention may be embodied in a CD ROM supplied to an individual for testing on a home or personal computer. Yet another example of the present invention is a system for delivering computer readable instructions such as transmission, over a signal transmission medium, of signals representative of instructions for testing in a convenient manner (e.g. the Internet).

The remote computer-implemented methods and apparatus described above are not limited to testing cognitive and/or perceptual abilities for monitoring efficacy and side effects of a therapy. The remote computer-implemented methods may indeed have a broad range of application outside of testing in conjunction with therapy program and may include cognitive and/or perceptual testing for any reason. By way of example, the present invention is also suitable to test individuals for cognitive skills and/or perceptual abilities to maintain a periodic reference of status at any given time. This reference may be useful in future endeavors as a basis for comparison, e.g. when the person is healthy compared to when they are unhealthy. The present invention is also suitable for periodic testing to assess the onset of a particular health condition. By way of example, the present invention is also suitable for individuals at high risk of Alzheimer's disease who take annual tests to assess disease onset or progression. This may advantageously save these individuals unwanted trips to a doctor's office for testing and may increase testing acceptability. The present invention is also suitable to remotely monitor progress of a degenerative disease or illness. In a specific embodiment, the remote computer-implemented testing is performed on a daily basis to evaluate progression of the degenerative disease or illness.

While this invention has been described in terms of several preferred embodiments, there are alterations, permutations, and equivalents which fall within the scope of this invention. Testing in accordance with the present invention may include any testing known in the art for administering cognitive and/or perceptual testing. By way of example, cognitive tests such as numerical reasoning, pattern recognition, or testing the ability to control with a dominant hand (i.e. using a computer game) are suitable for use with the present invention. In addition, perceptual tests such as auditory frequency detection, visual contrast discrimination, tactile manipulation, vestibular testing and tactile pattern recognition are also suitable for use with the present invention. The distinction between cognitive and/or perceptual testing is generally recognized in the art. Nevertheless, some tests may be variably thought of by individual practitioners as a cognitive test or a perceptual test. The present invention is not restricted by any limiting definitions of cognitive and/or perceptual testing and indeed covers both, as generally understood by one of ability in the art. It is intended that the following appended claims be interpreted as including all such alterations, permutations, and equivalents as fall within the true spirit and scope of the present invention.

What is claimed is:

1. A computer-implemented method for remotely administering perceptual testing on a human subject, said method being implemented using a computer network having a monitoring computer and a remote administering computer, said remote administering computer being geographically remote from said monitoring computer and local to said human subject, said method comprising:
   performing (a) and (b) a number of times effective to evaluate at least one perceptual ability of said human subject:
   a) administering, using a remote computer-implemented approach, at least one perceptual test to said human subject, and
   b) obtaining, using said remote administering computer, at least one performance response of said human subject in said at least one perceptual test;
   monitoring the obtained at least one performance response of said human subject in said at least one perceptual test, including monitoring for one of an efficacy of a therapy program and side effects of said therapy program;
   uploading testing information including said performance response from said administering computer via said computer network; and
   adapting said at least one perceptual test in response to said testing information.

2. The remote computer-implemented method of claim 1 wherein (a) and (b) are repeatedly performed to attain a number of times effective to evaluate said at least one perceptual ability of said human subject.

3. The remote computer-implemented method of claim 1 wherein (a) and (b) are performed once to attain a number of times effective to evaluate said at least one perceptual ability of said human subject.

4. The remote computer-implemented method of claim 1 further including administering at least one initial perceptual test to said human subject.

5. The remote computer-implemented method of claim 4 wherein said initial perceptual test includes a perceptual test that tests for a perceptual ability that is substantially affected by a therapy program to be administered to said human subject.

6. The remote computer-implemented method of claim 1 wherein (a) and (b) are performed on a daily basis.

7. The remote computer-implemented method of claim 6 wherein (a) and (b) are performed on a daily basis to evaluate a progression of one of a degenerative disease or illness.

8. The remote computer-implemented method of claim 1 wherein (a) and (b) are performed at substantially the same time each day.

9. The remote computer-implemented method of claim 1 further including monitoring the obtained performance responses of said human subject in said at least one perceptual test.

10. The remote computer-implemented method of claim 9 wherein said monitoring the obtained performance responses includes monitoring for discrepancies in at least one perceptual ability relative to an expected performance based on prior testing of a past human subject in said at least one perceptual test.

11. The remote computer-implemented method of claim 1 wherein (a) and (b) are repeated for a duration that is longer than the duration of a therapy program.

12. The remote computer-implemented method of claim 1 wherein said at least one initial perceptual test includes a perceptual initial test that may be adapted.

13. The remote computer-implemented method of claim 1 wherein adapting said at least one perceptual test includes altering at least one parameter of said at least one perceptual test.

14. The remote computer-implemented method of claim 1 wherein a different perceptual test is employed in different iterations of (a) and (b).

15. The remote computer-implemented method of claim 14 wherein the different perceptual test employed in different iterations of (a) and (b) is selected based on prior performance of the subject in a previous iteration of (a) and (b) for said at least one perceptual test.

16. The remote computer-implemented method of claim 1 further including uploading said testing information to a monitoring site.

17. The remote computer-implemented method of claim 16 further including transferring said testing information to another location other than said monitoring site.

18. The remote computer-implemented method of claim 1 further including building a database.

19. The remote computer-implemented method of claim 18 wherein the database includes data from initial perceptual testing, demographic information on said human subject, said at least one perceptual test and said performance response.

20. The remote computer-implemented method of claim 18 further including providing information from said database to said user.

21. The remote computer-implemented method of claim 20 wherein providing said information from said database to said user is used for self-evaluation by said user.

22. The remote computer-implemented method of claim 18 wherein the database is used in assessment of one of a biochemical based therapy program or a behavioral therapy program.

23. The remote computer-implemented method of claim 1 wherein said at least one perceptual test includes one of a visual test, an auditory test, vestibular test and a somatosensory test.

24. The remote computer-implemented method of claim 1 wherein said at least one perceptual test includes a pop-out test.

25. The remote computer-implemented method of claim 1 further including administering at least one initial perceptual test to said human subject before inception of said therapy program.

26. A computer readable medium including instructions for remotely administering perceptual testing on a human subject, said method being implemented using a computer network having a monitoring computer and a remote administering computer, said remote administering computer being geographically remote from said monitoring computer and local to said human subject, said instructions comprising:

instructions for performing (a) and (b) a number of times effective to evaluate at least one perceptual ability of said human subject:
  a) administering, using a remote computer-implemented approach, at least one perceptual test to said human subject, and
  b) obtaining, using said remote administering computer, a performance response of said human subject in said at least one perceptual test;

instructions for monitoring the obtained at least one performance response of said human subject in said at least one perceptual test, including monitoring for one of an efficacy of a therapy program and side effects of said therapy program;

instructions for uploading testing information including said performance response from said administering computer via said computer network; and instructions for adapting said at least one perceptual test in response to said testing information.

27. A computer-implemented method for delivering computer readable instructions for remotely administering perceptual testing on a human subject, said method being implemented using a computer network having a monitoring computer and a remote administering computer, said remote administering computer being geographically remote from said monitoring computer and local to said human subject, said instructions comprising:

transmitting, over a signal transmission medium, signals representative of instructions for performing (a) and (b) below a number of times effective to evaluate at least one perceptual ability of said human subject:
  a) administering, using a remote computer-implemented approach, at least one perceptual test to said human subject, and
  b) obtaining, using said remote administering computer, a performance response of said human subject in said at least one perceptual test;

transmitting, over a signal transmission medium, signals representative of instructions for monitoring the obtained at least one performance response of said human subject in said at least one perceptual test, including monitoring for one of an efficacy of a therapy program and side effects of said therapy program;

transmitting, over a signal transmission medium, signals representative of instructions for uploading testing information including said performance response from said administering computer via said computer network; and transmitting, over a signal transmission medium, signals representative of instructions for adapting said at least one perceptual test in response to said testing information.

* * * * *